United States Patent
Kim et al.

(10) Patent No.: US 10,150,795 B2
(45) Date of Patent: Dec. 11, 2018

(54) PEPTIDE HAVING ANTIMICROBIAL ACTIVITY AGAINST PATHOGENS AND ANTIMICROBIAL PEPTIDE COMPOSITION COMPRISING THE SAME

(71) Applicant: Hankuk University of Foreign Studies Research & Business Foundation, Gyeonggi-do (KR)

(72) Inventors: Yong Ae Kim, Gyeonggi-do (KR); Ji Sun Kim, Seoul (KR); Ji Ho Jeong, Gyeonggi-do (KR)

(73) Assignee: HANKUK UNIVERSITY OF FOREIGN STUDIES RESEARCH & BUSINESS FOUNDATION, Gyeonggi-do (KR)

( * ) Notice: Subject to any disclaimer, the term of this patent is extended or adjusted under 35 U.S.C. 154(b) by 0 days.

(21) Appl. No.: 15/512,193

(22) PCT Filed: May 25, 2016

(86) PCT No.: PCT/KR2016/005513
§ 371 (c)(1),
(2) Date: Mar. 17, 2017

(87) PCT Pub. No.: WO2017/188498
PCT Pub. Date: Nov. 2, 2017

(65) Prior Publication Data
US 2018/0170965 A1    Jun. 21, 2018

(30) Foreign Application Priority Data
Apr. 26, 2016   (KR) .................. 10-2016-0051073

(51) Int. Cl.
| | | |
|---|---|---|
| *A61K 38/00* | (2006.01) | |
| *A61K 38/08* | (2006.01) | |
| *A61K 38/10* | (2006.01) | |
| *C07K 7/08* | (2006.01) | |
| *C07K 7/06* | (2006.01) | |
| *C07K 16/12* | (2006.01) | |
| *C07K 4/12* | (2006.01) | |
| *C07K 14/47* | (2006.01) | |
| *A61P 31/04* | (2006.01) | |

(52) U.S. Cl.
CPC .............. *C07K 7/08* (2013.01); *A61P 31/04* (2018.01); *C07K 4/12* (2013.01); *C07K 7/06* (2013.01); *C07K 14/47* (2013.01); *A61K 38/00* (2013.01)

(58) Field of Classification Search
CPC . C07K 7/08; C07K 7/06; C07K 16/12; C07K 16/1203; C07K 16/1232; C07K 16/1214; C07K 16/1235; C07K 16/1267; C07K 16/1296; A61K 38/00; A61K 38/08; A61K 38/10
USPC .... 530/300, 327, 328; 514/2.3, 2.4, 2.7, 2.8, 514/21.5, 21.6
See application file for complete search history.

(56) References Cited

U.S. PATENT DOCUMENTS
2005/0118198 A1   6/2005  Pier et al.

FOREIGN PATENT DOCUMENTS
| | | |
|---|---|---|
| KR | 10-2010-0071769 | 6/2010 |
| KR | 10-2010-0123272 | 11/2010 |
| KR | 10-2012-0131399 | 12/2012 |
| KR | 10-2013-0078561 | 7/2013 |
| WO | 2013/108193 | 7/2013 |

OTHER PUBLICATIONS

Jiang et al, "NMR Structural Studies of Antimicrobial Peptides: LPcin Analogs," Biophysical Journal, Jan. 2016, 110: 423-430.*
English translation to KR 10-2012-0131399, pp. 1-13. Published Apr. 29, 2013.*
Zasloff, "Magainins, a class of antimicrobial peptides from Xenopus skin: Isolation, characterization of two active forms and partial cDNA sequence of a precursor", Proc. Natl. Acad. Sci. USA vol. 84, pp. 5449-5453, Aug. 1987.
Park et al., "A Novel Antimicrobial Peptide from Bufo bufo gargarizans", Biochemical and Biophysical Research Communications 218, 408-413 (1996).
Wang et al., "Cloning and expression of a hepcidin gene from a marine fish (Pseudosciaena crocea) and the antimicrobial activity of its synthetic peptide", Peptides 30 (2009) 638-646.

* cited by examiner

*Primary Examiner* — Julie Ha
(74) *Attorney, Agent, or Firm* — Michael Best & Friedrich LLP

(57) ABSTRACT

An antimicrobial peptide and an antimicrobial peptide composition comprising the same are provided. The antimicrobial peptide and the antimicrobial peptide composition have remarkably high antibacterial activity against gram-positive (+) and gram-negative (−) bacteria, compared to wild-type LPcin-I having an antimicrobial ability, which consists of a sequence of 23 amino acids. Also, the antimicrobial peptide can be useful in being easily synthesized and saving production costs since the antimicrobial peptide has a smaller number of amino acids, compared to the wild-type LPcin-I.

6 Claims, 2 Drawing Sheets

Specification includes a Sequence Listing.

PEPTIDE HAVING ANTIMICROBIAL ACTIVITY AGAINST PATHOGENS AND ANTIMICROBIAL PEPTIDE COMPOSITION COMPRISING THE SAME

TECHNICAL FIELD

This application claims priority to Korean Patent Application No. 10-2016-0051073, filed on Apr. 26, 2016, the disclosure of which is incorporated herein by reference in its entirety.

The present invention relates to a peptide having antimicrobial activity against pathogens and an antimicrobial peptide composition including the same, and more particularly, to a peptide having antimicrobial activity against pathogens, which is derived from an LPcin-I peptide whose antimicrobial ability is remarkably improved by deleting and/or substituting some amino acids in an LPcin-I peptide having an antimicrobial ability, and an antimicrobial peptide composition including the same.

BACKGROUND ART

Since cecropins, which are novel antimicrobial peptides from silkworm larva, were found in the results of research on defense mechanisms of insects against the microbial invasion, the importance of novel peptides as bioactive substances has been greatly recognized. The recent results of several years of research show that almost all higher organisms accumulate or secrete antimicrobial peptides in their bodies as defense measures against pathogenic microbes, separate from immune systems. Approximately 2,000 antimicrobial peptides have been found so far, and these peptides have been known to have different amino acid compositions in every discovered species but have similar mechanisms of action. Representative antimicrobial peptides known in the art include cecropins, magainins, bombinin, defensins, tachyplesin, and buforin. It was known that these antimicrobial peptides commonly consist of 17 to 24 amino acids, and have antimicrobial activity against prokaryotes or fungi as well as gram-negative and gram-positive bacteria, and are effective against cancer cells and viruses as well.

In particular, among the antimicrobial peptides, it was reported that a magainin is a peptide that has a composition of 23 amino acids and is separated from the skin of an amphibian (Zasloff, M., Proc. Natl. Acad. Sci. USA, 84, pp 5449-5453, 1987), and acts on human lung cancer cells as well as pathogens. Also, most of the antimicrobial peptides specifically act on cells to rapidly kill target cells, and largely exhibit activity spectra in a wide range (Park, C. B. et al., Biochem. Biophys. Res. Comm., 218, pp 408-413, 1996).

The antimicrobial peptides have advantages in that they 1) have potent antimicrobial activity against a wide range of microbes, 2) act on only pathogens invading from the outside without destroying host cells, and thus act as an antimicrobial substance that is not harmful to human bodies, 3) have a low probability to induce resistance because they have a mechanism of action completely different from those of the conventional antimicrobials which induce resistance in microbes, which was problematic, 4) may be mass-produced through gene manipulation because they have no secondary modification such as glycosylation, and 5) are highly industrially usable in the field of pharmaceuticals and food because they show high physicochemical stability with respect to heat, acids or alkalis.

The currently reported mechanisms of action of the antimicrobial peptides are mainly divided into two categories. First, a majority of the antimicrobial peptides have a mechanism of action in which the antimicrobial peptides increase the permeability of bacterial cell membranes to destroy a membrane potential and terminate cell metabolism. Second, a minority of the antimicrobial peptides have a potent mechanism of action in which the antimicrobial peptides invade bacterial cells and bind to DNA or RNA to inhibit transcription or translation.

Structural elements which are known to be important for these activities of the antimicrobial peptides may include the following: 1) an amphipathic helix, 2) a distribution of residues to stabilize the helix, 3) a distribution of basic residues, 5) a distribution of hydrophobic residues, 5) an interaction between charged residues and a dipole of the helix, and 6) a salt bridge between oppositely-charged residues.

Meanwhile, lactophoricin (LPcin-I) present in cow milk is an cationic and amphipathic peptide that consists of 23 amino acid residues, and corresponds to a carboxyl terminal 113 to 135 region of PP3. LPcin-I inhibits the growth of both gram-positive and gram-negative bacteria, but does not have a hemolytic action at a concentration of 200 µM or less. Unlike LPcin-I, LPcin-II corresponding to a $119^{th}$ to $135^{th}$ amino acid region of PP3 is known to have no antimicrobial functionality.

However, to commercialize the LPcin-I known to have an antimicrobial ability, there is an urgent demand to develop technology in which antimicrobial peptides consisting of shorter amino acid sequences are prepared so as to exhibit a higher antimicrobial ability than the wild-type LPcin-I and reduce production costs.

DISCLOSURE

Technical Problem

Therefore, the present invention is designed to solve the problems of the prior art, and it is an object of the present invention to provide a peptide having antimicrobial activity against pathogens, which has a shorter amino acid sequence than the wild-type lactophoricin (LPcin-I) antimicrobial peptide consisting of 23 amino acids and exhibit remarkably improved antimicrobial activity.

It is another object of the present invention to provide an antimicrobial composition including the antimicrobial peptide of the present invention as an active ingredient.

Technical Solution

To solve one of the above problems, the present invention provides a peptide represented by the following sequence [General Formula I] having antimicrobial activity against pathogens:

[General Formula I]
[(N-terminus)-N K V K E W $X^1$ K $X^2$ L K $X^3$ $X^4$ F $X^5$-(C-terminus)]

wherein $X^1$ is I or W, $X^2$ is Y when $X^1$ is I, and $X^2$ is W when $X^1$ is W;
$X^3$ is S or K;
$X^4$ is L or K; and
$X^5$ is S or K.

Also, the present invention provides a use of the peptide represented by the sequence [General Formula I] having antimicrobial activity against the pathogens.

According to one preferred embodiment of the present invention, the peptide may be a peptide from which $X^3 X^4 F X^5$ or $F X^5$ in General Formula I is deleted.

According to another preferred embodiment of the present invention, the peptide may consist of one amino acid sequence selected from the group consisting of SEQ ID NOs: 1 to 10.

To solve the other problem, the present invention provides an antimicrobial peptide composition including the antimicrobial peptide of the present invention as an active ingredient.

Also, the present invention provides a use of the antimicrobial peptide composition including the antimicrobial peptide as an active ingredient.

According to still another preferred embodiment of the present invention, the antimicrobial activity may be antimicrobial activity against one or more bacteria selected from the group consisting of *Staphylococcus aureus, Salmonella* spp., *Listeria innocua, Pseudomonas aeruginosa,* and *Escherichia coli.*

Advantageous Effects

The antimicrobial peptide of the present invention and the antimicrobial peptide composition including the antimicrobial peptide have remarkably high antibacterial activity against gram-positive (+) and gram-negative (−) bacteria, compared to wild-type LPcin-I having an antimicrobial ability and consisting of a sequence of 23 amino acids. Also, the antimicrobial peptide is easily delivered to a site in need thereof without being digested in vivo during a drug delivery process as the antimicrobial peptide has a shorter amino acid length. Also, the antimicrobial peptide can be useful in being easily synthesized and saving production costs since the antimicrobial peptide has a smaller number of amino acids, compared to the wild-type LPcin-I.

BEST MODE

Figure 1:
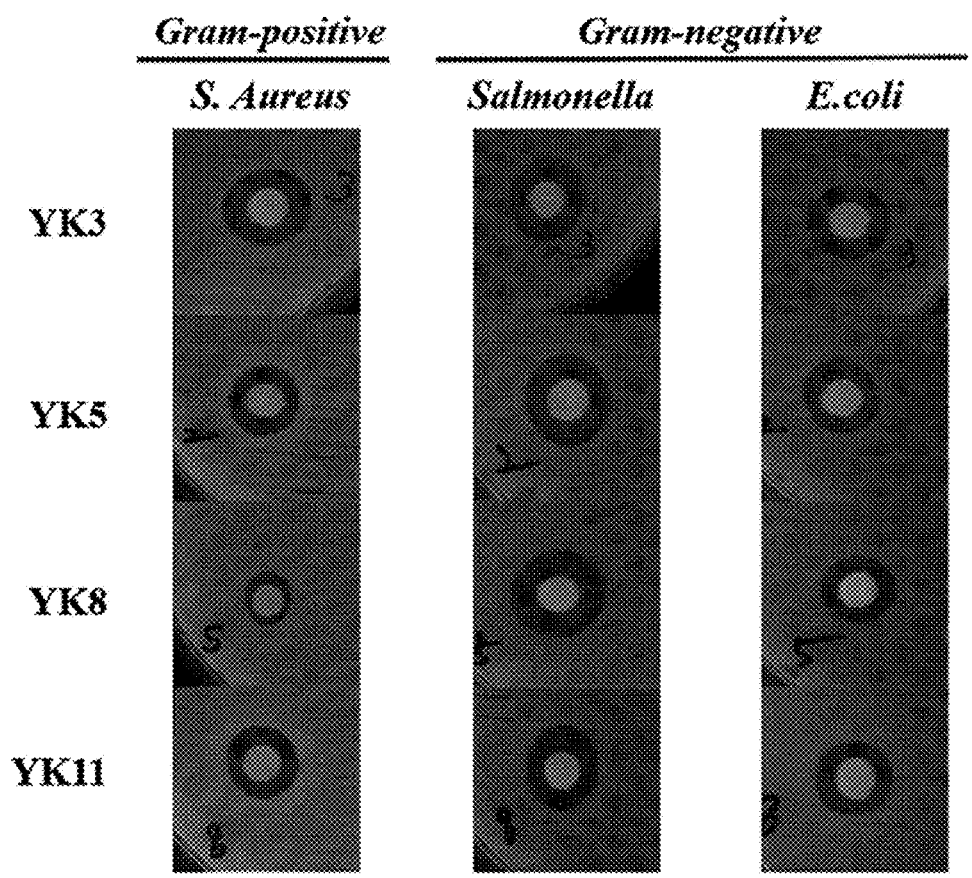
FIG. 1 is an image showing results of performing an antimicrobial activity test on three microbes, which include one gram-positive bacterium (*Staphylococcus aureus* ATCC 6538) and two gram-negative bacteria (*Salmonella* ATCC 19430 and *Escherichia coli* KCTC 1682).

Hereinafter, the present invention will be described in further detail.

As described above, lactophoricin (LPcin-I) present in cow milk is an cationic and amphipathic peptide that consists of 23 amino acid residues, and corresponds to a carboxyl terminal 113 to 135 region of PP3. LPcin-I inhibits the growth of both gram-positive and gram-negative bacteria, but does not have a hemolytic action at a concentration of 200 μM or less. However, to commercialize the LPcin-I known to have an antimicrobial ability, there is an urgent demand to develop technology in which antimicrobial peptides consisting of shorter amino acid sequences are prepared so as to exhibit a higher antimicrobial ability than the wild-type LPcin-1 and reduce production costs.

Therefore, to solve one of the above problems regarding to one exemplary embodiment of the present invention, the present invention provides a peptide represented by the following sequence [General Formula I] having antimicrobial activity against pathogens, thereby promoting a solution to the above problems. Accordingly, an antimicrobial peptide of the present invention and an antimicrobial peptide composition including the antimicrobial peptide have remarkably high antibacterial activity against gram-positive (+) and gram-negative (−) bacteria, compared to the wild-type LPcin-I which has an antimicrobial ability and consists of a sequence of 23 amino acids. Also, the antimicrobial peptide may be useful in being easily synthesized and saving production costs since the antimicrobial peptide has a smaller number of amino acids, compared to the wild-type LPcin-I:

[General Formula I]
[(N-terminus)-N K V K E W X$^1$ K X$^2$ L K X$^3$ X$^4$
F X$^5$-(C-terminus)]

wherein $X^1$ is I or W, $X^2$ is Y when $X^1$ is I, and $X^2$ is W when $X^1$ is W;
$X^3$ is S or K;
$X^4$ is L or K; and
$X^5$ is S or K.

The amino acids in the sequence used in the present invention are represented by the following abbreviations according to the IUPAC-IUB nomenclature:

Alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), and valine (V).

In General Formula I of the present invention, $X^1$ may be I, W, or a non-polar amino acid, $X^2$ is Y when $X^1$ is I and $X^2$ is W when $X^1$ is W.

Meanwhile, in the present invention, non-polar amino acids include glycine (G), alanine (A), valine (V), leucine (L), isoleucine (I), phenylalanine (F), tryptophan (W), methionine (M), cysteine (C), and proline (P). Polar amino acids include serine (S), threonine (T), tyrosine (Y), asparagine (N), and glutamine (Q). Acidic amino acids include aspartic acid (D), and glutamic acid (E), and basic amino acids include lysine (K), arginine (R), and histidine (H).

Meanwhile, according to one preferred embodiment of the present invention, the peptide may be a peptide in which $X^3 X^4 F X^5$ or $F X^5$ is deleted from the C-terminus thereof. Specifically, antimicrobial peptides set forth in SEQ ID NOs: 9 to 11 according to the present invention are antimicrobial peptides from which $F X^5$ is deleted, and an antimicrobial peptide set forth in SEQ ID NO: 12 is an antimicrobial peptide from which $X^3 X^4 F X^5$ is deleted. Such antimicrobial peptides set forth in SEQ ID NOs: 1 to 12 exhibit remarkably excellent antibacterial activity, compared to the wild-type LPcin-I (SEQ ID NO: 13) (see Experimental Example 2).

According to one preferred embodiment of the present invention, the peptide has any one amino acid sequence selected from the group consisting of amino acid sequences set forth in SEQ ID NO: 1 to 10, and thus may be very advantageous for reducing production costs and exhibiting excellent antibacterial activity (see Experimental Example 1). Most preferably, the antimicrobial peptides exhibiting excellent antibacterial activity in the present invention may be YK5 (SEQ ID NO: 3), YK8 (SEQ ID NO: 6), and YK11 (SEQ ID NO: 9) peptides.

The antimicrobial peptides YK5, YK8 and YK11 of the present invention are more economical because the antimicrobial peptides may effectively inhibit the five above-mentioned strains when present at a lower concentration, compared to YK3. Also, YK11 has an economical advantage in that YK11 may be commercially produced because YK11 has an amino acid sequence which is shorter by 2 mers than that of the YK3.

Meanwhile, according to one preferred embodiment of the present invention, the LPcin-I peptide set forth in SEQ ID NO: 13 and consisting of 23 amino acids may be prepared using a conventional peptide synthesis method, specifically, may be prepared using an automated peptide synthesizer or prepared by constructing a recombinant expression vector and purifying the recombinant expression vector. Korean Patent Application No. 2008-130593 which relates to a method of synthesizing an LPcin-I antimicrobial peptide using the recombinant expression vector is incorporated herein by reference in its entirety.

Also, the LPcin-I peptide may be synthesized by a Merrifield's liquid-solid method using 9-fluorenylmethoxycarbonyl (Fmoc) as a group for protecting an amino group (Merrifield, R B., J. Am. Chem. Soc., 85, 2149, 1963).

Also, according to one preferred embodiment of the present invention, the antimicrobial peptides having the amino acid sequences set forth in SEQ ID NOs: 1 to 10 may be prepared using conventional methods like the preparation of the antimicrobial peptide set forth in SEQ ID NO: 13. The antimicrobial peptides of the present invention thus prepared have high antimicrobial activity against gram-positive (+) and gram-negative (−) strains. In particular, the antimicrobial peptides have high antimicrobial activity against representative strains such as two gram-positive bacteria (*Listeria innocua* MC2 KCTC 3658 and *Staphylococcus aureus* ATCC 6538) and three gram-negative bacteria (*Pseudomonas aeruginosa* ATCC27853, *Salmonella* ATCC 19430, and *Escherichia coli* KCTC 1682), but the present invention is not limited thereto.

In addition, the present invention relates to an antimicrobial composition including the antimicrobial peptide as an active ingredient. The antimicrobial composition including the antimicrobial peptide of the present invention as an active ingredient may be effectively used for additives such as antimicrobial and antifungal agents, food preservatives, cosmetic preservatives, vulneraries, eye drops, and pharmaceutical preservatives.

For clinical administration, the antimicrobial peptide of the present invention may be parenterally administered, and may be used in the form of a general pharmaceutical preparation. The antimicrobial peptide of the present invention may be actually administered in the form of various parenteral formulations, and may be formulated using a diluent or excipient typically used in the art, such as a filler, a bulking agent, a binder, a wetting agent, a disintegrating agent, a surfactant, etc., when prepared into formulations. The preparations for parenteral administration may include a sterile aqueous solution, a non-aqueous solvent, a suspending agent, an emulsion, a lyophilized preparation, a suppository, etc. Vegetable oil such as propylene glycol, polyethylene glycol, and olive oil, an injectable ester such as ethyl oleate, and the like may be used as the non-aqueous solvent and the suspending agent. Witepsol, Macrogol, Tween 61, cacao butter, laurin butter, glycerogelatin, the like may be used as a base of the suppository.

Also, the antimicrobial peptide of the present invention may be used in combination with various carriers commercially available as drugs such as physiological saline or organic solvents, and carbohydrates such as glucose, sucrose or dextran, antioxidants such as ascorbic acid or glutathione, chelating agents, low-molecular-weight proteins, or other stabilizers may be used as drugs for enhancing stability or absorptivity.

The antimicrobial peptide of the present invention may be administered at an effective dose of 0.1 to 3 mg/kg, preferably 0.5 to 1 mg/kg, and may be administered once to three times a day.

The antimicrobial composition including the antimicrobial peptide of the present invention as an active ingredient may be administered to patients in the form of a bolus or at a single dose through infusion for a relatively short period of time, and may be administered according to the fractionated treatment protocol in which multiple doses are administered for a long period of time.

A concentration of the administered antimicrobial peptide according to the present invention may be determined in consideration of various factors such the age and health condition of a patient, and the like as well as a route of administration of a drug and the number of treatments. Therefore, a person having ordinary skill in the art may easily determine a proper effective dose when considering these factors.

Also, according to one preferred embodiment of the present invention, a feed composition including the antimicrobial peptide of the present invention as an active ingredient is provided. In this case, the feed composition may be included at an effective dose of 0.01 to 100 mg, based on 1 kg of the feed, and may be administered once to three times a day.

Hereinafter, the present invention will be described in further detail with reference to examples. However, it will be apparent to those skilled in the art that the following examples are just preferred examples for the purpose of illustration only and are not intended to limit the scope of the invention.

MODE FOR INVENTION

Example 1

Preparation of Novel Antimicrobial Peptide

Peptides having sequences listed in the following Table 1 were synthesized using an automated peptide synthesizer (Milligen 9050, Millipore, US), and the synthesized peptides were purely separated using preparative reversed-phase high-performance liquid chromatography (Shimadzu Prominence HPLC using Shiseido Capcell Pak C18 columns).

In the following Table 1, SEQ ID NO: 11 represents a sequence of a wild-type LPcin-I antimicrobial peptide having 23 amino acids, SEQ ID NOs: 1 to 6 represent sequences of the antimicrobial peptides which consist of 15 amino acids, and SEQ ID NOs: 7 to 9 represent sequences of the antimicrobial peptides which consist of 13 amino acids. Also, SEQ ID NO: 10 represents a sequence of the antimicrobial peptide which consists of 11 amino acids.

TABLE 1

| Peptide names | Amino acid sequences | SEQ ID NOs |
|---|---|---|
| YK3 (15-mer) | NKVKE WIKYL KSLFS | 1 |
| YK4 (15-mer) | NKVKE WWKWL KSLFS | 2 |
| YK5 (15-mer) | NKVKE WIKYL KSLFK | 3 |
| YK6 (15-mer) | NKVKE WIKYL KSKFS | 4 |
| YK7 (15-mer) | NKVKE WWKWL KSLFK | 5 |
| YK8 (15-mer) | NKVKE WIKYL KSKFK | 6 |
| YK9 (13-mer) | NKVKE WWKWL KSL | 7 |
| YK10 (13-mer) | NKVKE WIKYL KKL | 8 |
| YK11 (13-mer) | NKVKE WWKWL KKL | 9 |
| YK12 (11-mer) | NKVKE WWKWL K | 10 |
| LPcin-I (23-mer) | NTVKE TIKYL KSLFS HAFEV VKT | 11 |

Example 2

Experiment for Measurement of Antibacterial Activity

The antimicrobial activities of the 11 peptides of SEQ ID NOs: 1 to 11 synthesized in Example 1 were measured. Specifically, the antimicrobial activity against microbes was measured using brain heart infusion agar (Bacto™). The measurement was based on an agar disc diffusion test performed on five microbes including two gram-positive bacteria (*Listeria innocua* MC2 KCTC 3658 and *Staphylococcus aureus* ATCC 6538) and three gram-negative bacteria (*Pseudomonas aeruginosa* ATCC 27853, *Salmonella* ATCC 19430, and *Escherichia coli* KCTC 1682). Bacteria cultured overnight at 37° C. in 5 ml of a 3.7% brain heart infusion medium were prepared as the inoculum. A final concentration of a suspension was determined by adjusting a turbidity level of the suspension to a turbidity level (0.05) of a turbidity standard solution ($1 \times 10^8$ CFU/mL) using a spectrophotometer at 600 mu. 20 ml of brain heart infusion agar was plated on a cell culture plate having a diameter of 90 mm. 30 μl of a bacterial suspension was inoculated onto an agar plate using a sterile spreader. The inoculated agar plate was dried at room temperature for 30 minutes. Sterile 6 mm-thick filter paper (Whatman No. 1) was placed on a surface of the agar plate, and each of the antimicrobial peptides was dissolved in sterile water to a concentration of 10 mM, and 20 μl of the resulting solution was inoculated onto the filter paper. The solution was pre-diffused at room temperature for 30 minutes, and the plates were cultured at 37° C. for 24 hours. After 24 hours, the sensitivities of the antimicrobial peptides with respect to bacterial colonies were determined as a colony size and clearance in regions in which the growth of bacteria was inhibited by measuring growth inhibition diameters of the bacterial colonies around the filter paper. The sensitivity was obtained by repeating the measurement twice.

FIG. 1 is an image showing results of an agar disc diffusion test observed after 24 hours. Among these, an agar disc diffusion test was performed on YK3 as a peptide having antimicrobial activity for comparison with novel peptides using the method disclosed in Korean Patent Application No. 2011-0049538.

Example 3

Cytotoxicity Experiment

A cytotoxicity experiment was performed by a test method using a Cyto X™ cell viability assay kit (LPS SOLUTION). A 96-well cell culture plate was purchased from Corning, and mammalian cell lines were purchased from the American Type Culture Collection (ATCC). Also, the CytoX™ cell viability assay kit was purchased from LPS SOLUTION.

As an experimental method, stored frozen cells were thawed, cultured in a DMEM or RP 11640 medium supplemented with 10% FBS, and then sub-cultured at intervals of 2 to 3 days until a density of the cells reached 80 to 90%. For this experiment, the cells were detached by treating the cells with trypsin-EDTA, and then divided into wells of a 96-well plate so that the number of the cells amounted to 10,000 cells. Thereafter, the cells were cultured at 37° C. for 24 hours in a $CO_2$ incubator. Each of the prepared peptides was diluted with DMSO to concentrations of 10, 1, 0.1, 0.01, and 0.001 mM, and then diluted at 1:100 by adding 1 μl of DMSO or each of the prepared peptides to each well. Then, the cells were cultured at 37° C. for 24 hours in a $CO_2$ incubator. To measure cytotoxicity, 10 μl of each of the peptides prepared using the Cyto X™ cell viability assay kit (LPS SOLUTION) was added to each well. The cells were cultured at 37° C. for 1 to 4 hours in a $CO_2$ incubator, and an optical density was measured at 450 nm using a microplate reader. Then, the measured optical density was calculated as a percentage of a value measured for DMSO, and a graph was plotted using GraphPad Prism 5. Then, an $IC_{50}$ value was calculated. The $IC_{50}$ values of the four peptides (YK3, YK5, YK8, and YK11) in various mammalian cell lines are as listed in the following Table 2. When each of the $IC_{50}$ values of the four peptides in each cell line was greater than or equal to 10 μM, the peptides were judged to have no general cytotoxicity. As a result, it was confirmed that the four peptides were safe with respect to general cytotoxicity.

In particular, when a CHO-K1 cell line was treated with each of the four peptides, the YK3 peptide had an $IC_{50}$ value at 56.2 μM, and the YK5, YK8 and YK11 peptides had a respective $IC_{50}$ value at 57.0, 71.9 and 86.8 μM, which were higher than the $IC_{50}$ value of the YK3 peptide. That is, it was confirmed that the YK5, YK8 and YK11 peptides exhibited lower cytotoxicity than the YK3 peptide.

TABLE 2

Measurement results of cytotoxicity

| | $IC_{50}$ (μM) | | | | |
|---|---|---|---|---|---|
| Compounds | VERO | HFL-1 | L929 | NIH3T3 | CHO-K1 |
| YK3 | 99.1 | 94.0 | >100 | 76.0 | 56.2 |
| YK5 | >100 | >100 | >100 | >100 | 57.0 |
| YK8 | >100 | >100 | >100 | >100 | 71.9 |
| YK11 | 83.7 | >100 | >100 | 96.6 | 86.8 |

Example 4

Experiment for Measuring Minimal Inhibitory Concentration

An antimicrobial assay was performed by measuring a minimal inhibitory concentration (MIC) value using a standard broth microdilution method. The antimicrobial activity of each of the peptides was measured using two gram-positive bacteria (*Listeria innocua* MC2 KCTC 3658 and *Staphylococcus aureus* ATCC 6538) and three gram-negative bacteria (*Pseudomonas aeruginosa* ATCC 27853, *Salmonella* ATCC 19430, and *Escherichia coli* KCTC 1682). 50 µl of each of the five bacterial strains were prepared, mixed with 5 ml of 3.7% BHI, and then cultured overnight under conditions of 37° C. and 240 rpm. Thereafter, 50 µl of each of the cultured bacterial strains was mixed with 5 ml of 3.7% BHI, and cultured for 2 hours under conditions of 37° C. and 240 rpm. Each of the cultured bacterial strains was diluted with a 0.037% BHI solution to a concentration of $1 \times 10^8$ CFU/ml.

A dissolved synthetic peptide was diluted twofold, stepwise, with BHIB in a 96 well-plate. 5 µl of each of the strains prepared through dilution was mixed with 100 µl of the synthetic peptide at various concentrations in a 96-well plate (a microreader plate), and incubated at 37° C. for 12 hours while stirring. After the incubation, a change in optical density at 600 nm was measured using Microplate Reader Multiskan FC (Thermo Scientific, Waltham, Mass., USA), and a range of the MIC was set as the lowest concentration of a peptide in which the growth of bacteria starts to be inhibited. In addition to the MIC, a half maximal inhibitory concentration ($IC_{50}$) at which the growth of bacteria reaches 50% compared to the control was determined. As a solvent control, a mixture obtained by mixing 100 µl of a BHIB solution having no peptide with 5 µl of a bacterial strain was tested in the same manner as in the experimental groups. In this case, this experiment was repeatedly performed in triplicate for the accuracy of the experiment.

Figure 2:
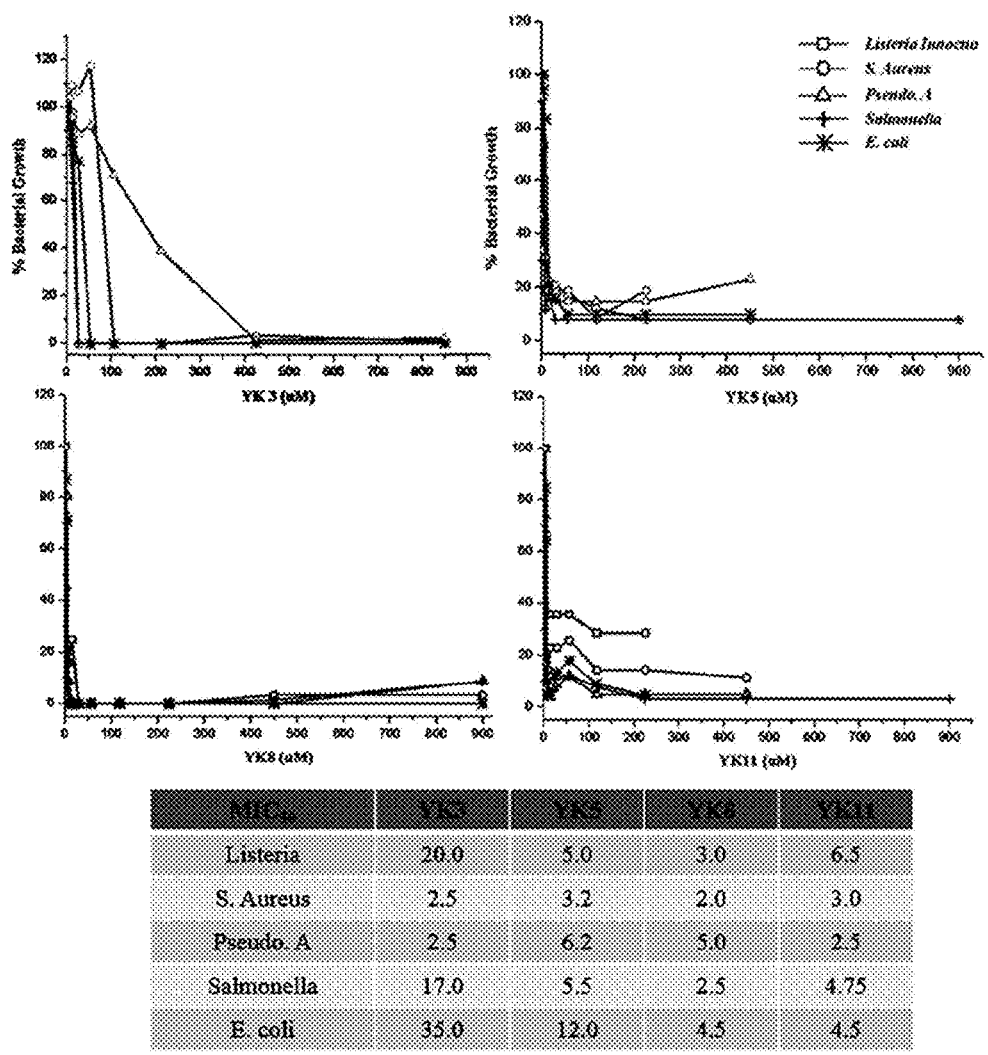
FIG. 2 is a set of a graph and a table obtained by measuring minimal inhibitory concentrations of two gram-positive bacteria (*Listeria innocua* MC2 KCTC 3658 and *Staphylococcus aureus* ATCC 6538) and three gram-negative bacteria (*Pseudomonas aeruginosa* ATCC 27853, *Salmonella* ATCC 19430, and *Escherichia coli* KCTC 1682).

As a result, it was revealed that all the peptides had antibacterial activity against the pathogens used in this experiment, as shown in FIG. 2. In particular, it was revealed that the YK5, YK8 and YK11 peptides had effective antibacterial activity against the five strains when used at a low concentration, compared to the YK3 peptide.

TABLE 3

Experimental peptide information

|  | Peptide | Amino acid sequence | Molecular weight | SEQ ID NO |
|---|---|---|---|---|
| 15-mers | YK3 | NKVKE WIKYL KSLFS | 1883.2 | 1 |
|  | YK5 | NKVKE WIKYL KSLFK | 1883.2 | 3 |
|  | YK8 | NKVKE WIKYL KSKFK | 1939.2 | 6 |
| 13-mer | YK11 | NKVKE WWKWL KKL | 1786.2 | 9 |

INDUSTRIAL APPLICABILITY

As described above, the antimicrobial peptide prepared in the present invention has a remarkable antibacterial effect against both of gram-positive and gram-negative bacteria and is not harmful to human bodies, and thus can be effectively used for feed additives, food preservatives, cosmetic and pharmaceutical preservatives, wound healing promoters, vulneraries, mouthwash, and eye drops.

The invention claimed is:

1. A peptide represented by the following sequence [General Formula I] having antimicrobial activity against pathogens:

[General Formula I]
[(N-terminus)-N K V K E W $X^1$ K $X^2$ L K $X^3$ $X^4$ F $X^5$-(C-terminus)]

wherein $X^1$ is I or W, $X^2$ is Y when $X^1$ is I, and $X^2$ is W when $X^1$ is W;

$X^3$ is S or K;

$X^4$ is L or K; and $X^5$ is S or K, wherein the sequence of the peptide is not NKVKEWIKYLKSLFS (SEQ ID NO: 1).

2. The peptide of claim 1, wherein the peptide is a peptide from which $X^3$ $X^4$ F $X^5$ or F $X^5$ in General Formula I is deleted.

3. The peptide of claim 1, wherein the peptide consists of any one amino acid sequence selected from the group consisting of SEQ ID NOs: 2 to 10.

4. An antimicrobial peptide composition comprising the antimicrobial peptide of any one of claims 1 to 3 as an active ingredient.

5. The antimicrobial peptide composition of claim 4, wherein the antimicrobial activity is antimicrobial activity against one or more bacteria selected from the group consisting of *Staphylococcus aureus, Salmonella* spp., *Listeria innocua, Pseudomonas aeruginosa*, and *Escherichia coli*.

6. A peptide represented by the following sequence [General Formula I] having antimicrobial activity against pathogens:

[General Formula I]
[(N-terminus)-
N K V K E W $X^1$ K $X^2$ L K $X^3$ $X^4$ F $X^5$-(C-terminus)]

wherein $X^1$ is I or W, $X^2$ is Y when $X^1$ is I, and $X^2$ is W when $X^1$ is W;

$X^3$ is S or K;

$X^4$ is L or K; and $X^5$ is S or K, and wherein the peptide is a peptide from which $X^3$ $X^4$ F $X^5$ or F $X^5$ in General Formula I is deleted.

* * * * *

SEQUENCE LISTING

```
<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: YK3 (15mer)

<400> SEQUENCE: 1

Asn Lys Val Lys Glu Trp Ile Lys Tyr Leu Lys Ser Leu Phe Ser
 1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: YK4 (15mer)

<400> SEQUENCE: 2

Asn Lys Val Lys Glu Trp Trp Lys Trp Leu Lys Ser Leu Phe Ser
 1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: YK5 (15mer)

<400> SEQUENCE: 3

Asn Lys Val Lys Glu Trp Ile Lys Tyr Leu Lys Ser Leu Phe Lys
 1               5                   10                  15
```

<210> SEQ ID NO 4
<211> LENGTH: 15
<212> TYPE: PRT
<213> ORGANISM: Artificial Sequence
<220> FEATURE:
<223> OTHER INFORMATION: YK6 (15mer)

<400> SEQUENCE: 4

Asn Lys Val Lys Glu Trp Ile Lys Tyr Leu Lys Ser Lys Phe Ser
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: YK7 (15mer)

<400> SEQUENCE: 5

Asn Lys Val Lys Glu Trp Trp Lys Trp Leu Lys Ser Leu Phe Lys
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: YK8 (15mer)

<400> SEQUENCE: 6

Asn Lys Val Lys Glu Trp Ile Lys Tyr Leu Lys Ser Lys Phe Lys
 1               5                  10                  15

<210> SEQ ID NO 7
<211> LENGTH: 13
<212> TYPE: PRT
<213> ORGANISM: Artificial Sequence
<220> FEATURE:
<223> OTHER INFORMATION: YK9 (13mer)

<400> SEQUENCE: 7

Asn Lys Val Lys Glu Trp Trp Lys Trp Leu Lys Ser Leu
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: YK10 (13mer)

<400> SEQUENCE: 8

Asn Lys Val Lys Glu Trp Ile Lys Tyr Leu Lys Lys Leu
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: YK11 (13mer)

<400> SEQUENCE: 9

Asn Lys Val Lys Glu Trp Trp Lys Trp Leu Lys Lys Leu
 1               5                  10

```
<210> SEQ ID NO 10
<211> LENGTH: 11
<212> TYPE: PRT
<213> ORGANISM: Artificial Sequence
<220> FEATURE:
<223> OTHER INFORMATION: YK12 (11mer)

<400> SEQUENCE: 10

Asn Lys Val Lys Glu Trp Trp Lys Trp Leu Lys
 1               5                  10

<210> SEQ ID NO 11
<211> LENGTH: 23
<212> TYPE: PRT
<213> ORGANISM: Artificial Sequence
<220> FEATURE:
<223> OTHER INFORMATION: LPcin-1 (23mer)

<400> SEQUENCE: 11

Asn Thr Val Lys Glu Thr Ile Lys Tyr Leu Lys Ser Leu Phe Ser His
 1               5                  10                  15

Ala Phe Glu Val Val Lys Thr
            20
```